(12) United States Patent
Fehr et al.

(10) Patent No.: US 9,259,309 B2
(45) Date of Patent: Feb. 16, 2016

(54) OPHTHALMIC DEVICES AND METHODS WITH APPLICATION SPECIFIC INTEGRATED CIRCUITS

(75) Inventors: Jean-Noel Fehr, Bern (CH); Walter Doll, Bern (CH); Urban Schnell, Bern (CH)

(73) Assignee: ELENZA, INC., Roanoke, CA (US)

( * ) Notice: Subject to any disclaimer, the term of this patent is extended or adjusted under 35 U.S.C. 154(b) by 152 days.

(21) Appl. No.: 13/805,612

(22) PCT Filed: Jun. 17, 2011

(86) PCT No.: PCT/US2011/040896
§ 371 (c)(1),
(2), (4) Date: Mar. 13, 2013

(87) PCT Pub. No.: WO2011/163080
PCT Pub. Date: Dec. 29, 2011

(65) Prior Publication Data
US 2014/0148899 A1    May 29, 2014

Related U.S. Application Data

(60) Provisional application No. 61/356,619, filed on Jun. 20, 2010.

(51) Int. Cl.
*A61F 2/16* (2006.01)
(52) U.S. Cl.
CPC .................. *A61F 2/1624* (2013.01)
(58) Field of Classification Search
USPC ....................................................... 623/6.22
See application file for complete search history.

(56) References Cited

U.S. PATENT DOCUMENTS

| 4,300,818 A | 11/1981 | Schachar |
| 4,309,603 A | 1/1982 | Stauffer |
| 4,373,218 A | 2/1983 | Schachar |
| 4,466,703 A | 8/1984 | Nishimoto |
| 4,601,545 A | 7/1986 | Kern |

(Continued)

OTHER PUBLICATIONS

International Search Report and Written Opinion received in International Application No. PCT/US2011/040896 dtd Oct. 18, 2011.

(Continued)

*Primary Examiner* — David H Willse
*Assistant Examiner* — Tiffany Shipmon
(74) *Attorney, Agent, or Firm* — Foley & Lardner LLP

(57) ABSTRACT

Ophthalmic devices with dynamic electro-active elements offer variable optical power and/or depth of field that restore lost accommodation in individuals suffering from presbyopia or aphakia. An illustrative device senses physiological processes indicative of the accommodative response and actuates a dynamic electro-active element to provide the desired change in optical power and/or depth of field. The illustrative device includes two application-specific integrated circuits (ASICs) for processing the accommodative response and actuating the electro-active element: a high-voltage ASIC that steps up a low voltage from a power supply to a higher voltage suitable for actuating the electro-active element, and another ASIC that operates at low voltage (and therefore consumes little power) and controls the operating state of the high-voltage ASIC. Because each ASIC operates at the lowest possible voltage, the illustrative ophthalmic device dissipates less power than other ophthalmic devices.

19 Claims, 16 Drawing Sheets

(56) References Cited

U.S. PATENT DOCUMENTS

| | | | |
|---|---|---|---|
| 4,787,903 | A | 11/1988 | Grendahl |
| 5,066,301 | A | 11/1991 | Wiley |
| 5,653,751 | A | 8/1997 | Samiy et al. |
| 5,712,721 | A | 1/1998 | Large |
| 6,200,342 | B1 | 3/2001 | Tassignon |
| 6,282,449 | B1 | 8/2001 | Kamerling et al. |
| 6,619,799 | B1 | 9/2003 | Blum et al. |
| 6,638,304 | B2 | 10/2003 | Azar |
| 6,706,066 | B1 | 3/2004 | Zhou et al. |
| 6,790,232 | B1 | 9/2004 | Lang |
| 7,041,133 | B1 | 5/2006 | Azar |
| 7,581,124 | B1 | 8/2009 | Jacobson et al. |
| 7,926,940 | B2 | 4/2011 | Blum et al. |
| 7,964,833 | B2 | 6/2011 | Holladay |
| 2006/0095128 | A1 | 5/2006 | Blum et al. |
| 2008/0221555 | A1 | 9/2008 | Sheppard et al. |
| 2009/0033863 | A1* | 2/2009 | Blum .................... A61F 2/14 351/159.34 |
| 2009/0069648 | A1* | 3/2009 | Irazoqui et al. .............. 600/302 |
| 2009/0264966 | A1 | 10/2009 | Blum et al. |
| 2010/0004741 | A1 | 1/2010 | Gupta et al. |
| 2010/0042209 | A1 | 2/2010 | Guarnieri |
| 2010/0110372 | A1* | 5/2010 | Pugh et al. .................... 351/177 |
| 2010/0148744 | A1* | 6/2010 | Kresse et al. ................ 323/313 |

OTHER PUBLICATIONS

Tang, T.B. et al., Implementation of Wireless Power Transfer and Communications for an Implantable Ocular Drug Delivery System, IET Nanobiotechnol., 2008, vol. 2, No. 3, pp. 72-79.

Bishop, Peter, A Tradeoff Between Microcontroller, DSP, FPGA and ASIC Technologies, EE Times, published Feb. 2009, 5 pages http://www.eetimes.com/document.asp?doc_id=1275272&.

Patent Examination Report No. 1 dated Sep. 4, 2015, received in corresponding Australian application No. 2011271278, 3 pages.

* cited by examiner

OPHTHALMIC DEVICES AND METHODS WITH APPLICATION SPECIFIC INTEGRATED CIRCUITS

CROSS REFERENCE TO RELATED APPLICATIONS

The present application is a National Stage of International Application No. PCT/US2011/040896 filed on Jun. 17, 2011, which claims the benefit of U.S. Provisional Patent Application No. 61/356,619 filed on Jun. 20, 2010, the entire disclosures of which are incorporated herein by reference.

BACKGROUND

There are two major conditions that affect an individual's ability to focus on near and intermediate distance objects: presbyopia and pseudophakia. Presbyopia is the loss of accommodation of the crystalline lens of the human eye that often accompanies aging. In a presbyopic individual, this loss of accommodation first results in an inability to focus on near distance objects and later results in an inability to focus on intermediate distance objects. It is estimated that there are approximately 90 million to 100 million presbyopes in the United States. Worldwide, it is estimated that there are approximately 1.6 billion presbyopes.

The standard tools for correcting presbyopia are reading glasses, multifocal ophthalmic lenses, and contact lenses fit to provide monovision. Reading glasses have a single optical power for correcting near distance focusing problems. A multifocal lens is a lens that has more than one focal length (i.e., optical power) for correcting focusing problems across a range of distances. Multifocal optics are used in eyeglasses, contact lenses, and intra-ocular lenses (IOLs). Multifocal ophthalmic lenses work by means of a division of the lens's area into regions of different optical powers. Multifocal lenses may be comprised of continuous surfaces that create continuous optical power as in a Progressive Addition Lens (PAL). Alternatively, multifocal lenses may be comprised of discontinuous surfaces that create discontinuous optical power as in bifocals or trifocals. Contact lenses fit to provide monovision are two contact lenses having different optical powers. One contact lens is for correcting mostly far distance focusing problems and the other contact lens is for correcting mostly near distance focusing problems.

Pseudophakia is the replacement of the crystalline lens of the eye with an IOL, usually following surgical removal of the crystalline lens during cataract surgery. For all practical purposes, an individual will get cataracts if he or she lives long enough. Furthermore, most individuals with cataracts will have a cataract operation at some point in their lives. It is estimated that approximately 1.2 million cataract surgeries are performed annually in the United States. In a pseudophakic individual, the absence of the crystalline lens causes a complete loss of accommodation that results in an inability to focus on either near or intermediate distance objects.

Conventional IOLs are monofocal, spherical lenses that provide focused retinal images for far objects (e.g., objects over two meters away). Generally, the focal length (or optical power) of a spherical IOL is chosen based on viewing a far object that subtends a small angle (e.g., about seven degrees) at the fovea. Unfortunately, because monofocal IOLs have a fixed focal length, they are not capable of mimicking or replacing the eye's natural accommodation response. Fortunately, ophthalmic devices with electro-active elements, such as liquid crystal cells, can be used to provide variable optical power as a substitute for the accommodation of an damaged or removed crystalline lens. For example, electro-active elements can be used as shutters that provide dynamically variable optical power as disclosed in U.S. Pat. No. 7,926,940 to Blum et al., which is incorporated herein by reference in its entirety.

SUMMARY

Embodiments of the disclosed technology include an implantable ophthalmic device and associated method of operating an implantable ophthalmic device with a high-voltage application-specific integrated circuit (ASIC) and a low-voltage ASIC operably coupled to the high-voltage ASIC. The high-voltage ASIC is configured to actuate an electro-active element at a first voltage, the low-voltage ASIC is configured to (i) regulate the high-voltage ASIC and (ii) operate at a second voltage lower than the first voltage. For instance, the low-voltage ASIC may be configured to regulate the high-voltage ASIC by causing the high-voltage ASIC to transition from an idle state to an operational state. In some cases, the first voltage is about 5 volts or less and the second voltage is about 5 volts to about 11 volts.

An illustrative implantable ophthalmic device may further include a power supply that supplies current to at least one of the high-voltage and low-voltage ASICs at a power supply voltage equal to or less than the second voltage. A switch enables current flow from the power supply to the high-voltage ASIC in response to a signal from the low-voltage ASIC. Optionally, a power-on reset block resets the high-voltage ASIC in response to actuation of the switch. A charge pump in the high-voltage ASIC can be used to transform the power supply voltage to the first voltage.

In some embodiments, the implantable ophthalmic device has one or more batteries that act as the power supply. A battery charger operably coupled to the battery charges the battery, e.g., by rectifying an rf voltage inductively coupled to the device by a radio-frequency (rf) antenna. A resonating capacitor in series with the rf antenna may provide an impedance for altering power transfer characteristics of the rf antenna, and a tuner can be used to trim the resonating capacitor. The battery charger may charge the battery by (i) charging the battery at a constant current until the battery reaches a predetermined voltage; and (ii) charging the battery at a constant voltage for a predetermined time after the battery reaches the predetermined voltage. The constant current can be about 120 µA to about 180 µA, and the predetermined voltage can be about 1.6 V to about 1.8 V.

Alternatively, the power supply may be or include a solar cell that generates a current for powering the high-voltage ASIC and/or the low-voltage ASIC.

In further embodiments, at least one of the high-voltage and low-voltage ASICs includes a nonvolatile memory configured to store information for actuating the electro-active element and/or a programmable logic controller to determine an actuation state of the electro-active element based on an accommodation signal representative of an accommodative response of a patient's eye. The accommodation signal may be converted from an analog signal by an analog-to-digital converter (ADC) that, optionally, compares the analog signal to a reference signal from a bandgap block that is independent of both temperature and a power supply voltage.

In exemplary embodiments, one or both ASICs may have a length of about 2 mm or less or and a width of about 2 mm or less. The ASICs can also be hermetically sealed.

In yet another embodiment, the implantable ophthalmic device includes a power supply configured to supply current at a first voltage. A charge pump that is operably coupled to the power supply transforms the first voltage to a second voltage that is both greater than the first voltage and suitable for actuating an electro-active element. A battery charger charges the battery (i) at a constant current until the battery reaches a predetermined voltage; and (ii) at a constant voltage for a predetermined time after the battery reaches the predetermined voltage.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The accompanying drawings, which are incorporated in and constitute a part of this specification, illustrate embodiments of the invention and together with the description serve to explain principles of the invention.

DETAILED DESCRIPTION

Figure 1:
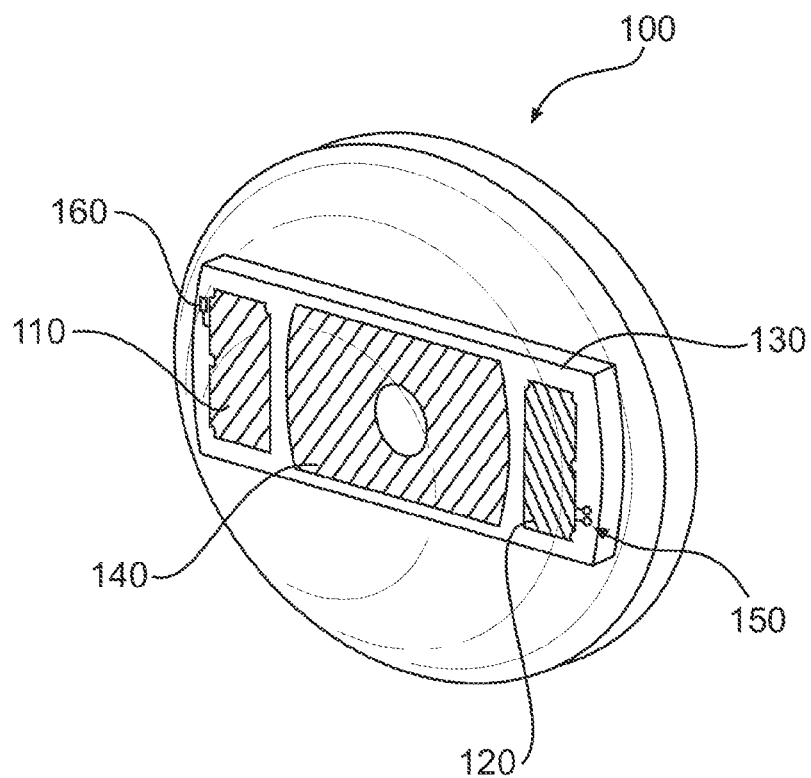
FIG. 1 is a diagram of an implantable ophthalmic device that includes a rechargeable battery, first application-specific integrated circuit (ASIC), second ASIC, and electro-active element.

Presently preferred embodiments of the invention are illustrated in the drawings. An effort has been made to use the same or like reference numbers to refer to the same or like parts.

Ophthalmic Devices with Application-Specific Integrated Circuits

Electro-active elements, such as those used in implantable and wearable ophthalmic devices, require operating voltages of about 5-11 V (e.g., about 9 V). These operating voltages are much greater than the 4 V or less typically provided by batteries, solar cells, or other power supplies suitable for use in implantable or wearable ophthalmic devices, which are typically only a few millimeters in diameter and thickness. A dedicated driver circuit can be used to step up the power supply voltage to a voltage high enough to drive an electro-active element, but dedicated driver circuit take up additional space, which increases the size of the ophthalmic device, and dissipate power, which decreases the usable lifetime of the ophthalmic device. Alternatively, all the electronics in the ophthalmic device can be operated at the same voltage as the electro-active element; however, this leads to increased heat dissipation due to power losses associated with stepping up the voltage from the power supply. As understood by those of skill in the art, increased heat dissipation is undesirable because it can lead to damage to the eye.

The ophthalmic devices disclosed herein each use two separate application-specific integrated circuits (ASICs) to provide all the necessary functionality for actuating an electro-active element in a small area and with minimal power dissipation. The first ASIC, which operates at relatively low voltage, e.g., about 4 V, provides functions such as data storage (memory), battery charging, etc. The second ASIC, which operates at relatively high voltage, e.g., 5-11 V, includes a charge pump that steps up the voltage from a power supply, such as a 1.4 V lithium-ion battery, to the 5-11 V actuation voltage of an electro-active cell. Because most of the electronics operate at low voltage, they consume less power, which increases the useful battery life (and the useful life of the device itself), e.g., to about twenty years or more. In addition, charge pumps consume less power and require less area (i.e., they have smaller footprints) than other DC-DC power converters, which makes it possible to reduce the size and power consumption of the second ASIC. Charge pumps also do not require the expensive inductors or additional semiconductors used in other DC-DC converters.

In some exemplary devices, the functions (and associated functional components) are partitioned among the first (low-voltage) ASIC and second (high-voltage) ASIC as follows. The first ASIC includes the functional blocks that are powered by a radio-frequency (rf) field, including the rf communication section (antenna), parts of the power management, and the battery charging. The second ASIC includes the functional blocks that are associated with therapy. These therapy functional blocks may be powered by one or more batteries. The first and second ASICs communicate via a serial communication interface, which may be housed on the second ASIC and powered through the first ASIC.

The first ASIC regulates the second ASIC. In other words, the first ASIC controls the second ASIC's operational state by initiating "wake-up," i.e., by causing the second ASIC to transition from an idle (sleep) state in which the second ASIC does not actuate or power the electro-active element or consume much power to an operational state in which the second ASIC steps up the battery voltage and/or actuates or powers the electro-active element. By controlling the operating state of the second (high-voltage) ASIC with the first (low-voltage) ASIC, the ophthalmic device consumes less power than other ophthalmic devices that offer similar functionality to the patient.

The second ASIC may also include a battery voltage level monitor which samples the battery voltage in a periodic fashion while the second ASIC is in both the idle and operational states. When the battery level monitor senses that the battery voltage has dropped below a predetermined threshold, e.g., due to self-discharge, a switch (e.g., a latch element, such as an R-S flip-flop) in the second ASIC opens, disconnecting the second ASIC from the battery to stop further discharge of the battery. Other features for reducing current consumption (and extending the device lifetime) include operating the ASICs at a low clock frequency, making as few gate state transitions as possible, and intermittently enabling analog functional sections whenever possible.

FIG. 1 shows an exemplary implantable ophthalmic device 100, such as an IOL, for use in dynamically correcting or adjusting a patient's vision. The device 100 includes an power supply—in this case, a rechargeable battery 130—coupled to a first ASIC 110 and a second ASIC 120. The battery 130 provides current at a relatively low voltage, e.g., about 4 V or less, to both ASICs 110 and 120. The second ASIC 120 is coupled to an electro-active element 140 that operates at a relatively high voltage, e.g., about 5 V to about 11 V. The electro-active element 140 provides a dynamically variable optical power and/or depth of field that adds to the (optional) static optical power provided by the device's curved surface. In this case, the electro-active element 140 acts as a variable diameter aperture that opens and closes in response to accommodative triggers to increase or decrease the depth of field. The device 100 may also include a sensor 150 for detecting the eye's accommodative response. The electronics can be embedded or otherwise hermetically sealed inside the device 100 itself, which may be molded of glass, resin, plastic, or any other suitable material.

Figure 2:
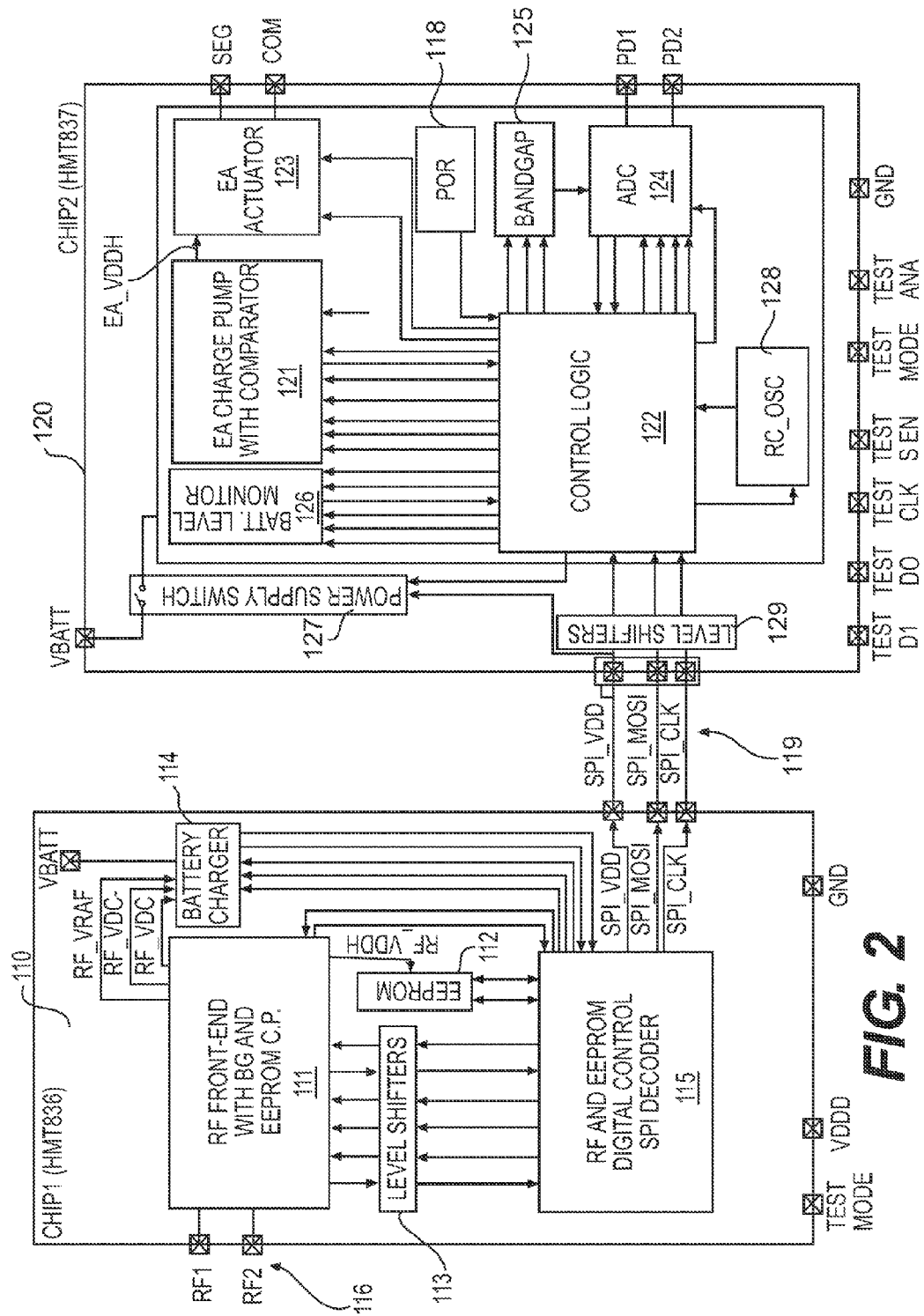
FIG. 2 illustrates first and second ASICs suitable for use in the implantable ophthalmic device of FIG. 1.

FIG. 2 shows the first ASIC 110 and second ASIC 120 in greater detail. The first ASIC 110 stores (i.e., maintains) settings for the electro-active element 140 in nonvolatile memory 112, such as an electrically erasable programmable read-only memory (EEPROM) or other suitable memory. The settings for the electro-active element 140, which correspond to different accommodative responses, may be loaded onto the memory 112 via one or more radio frequency (rf) antennas 160 (FIG. 1) that drive an rf front end 111. For example, the patient may query, actuate, and/or update the ophthalmic device with a wireless remote control that transmits data at a frequency received by the rf antenna 160. The rf antenna 160 may also be used to charge the power supply as described below. Level shifters 113 translate signals from the rf front end 111 to logic levels suitable for interpretation by a digital control and serial/parallel interface (SPI) decoder 115 that retrieve information from the memory 111 and controls a battery charger 114 (described below). The digital control and SPI decoder 115 also connects to the second ASIC 120 via SPI links 119.

Level shifters 129 in the second ASIC 120 translate digital signals from the first ASIC 110 to logic levels that used by a programmable logic controller (PLC) 122 in the second ASIC 120. A power supply switch 127 couples the first and second ASICs 110, 120 to the battery 130, and a battery level monitor 126 coupled to the battery 130 via the switch monitors the voltage supplied by the battery 130. A power-on reset block 118 resets the second ASIC 120 when the power supply switch 127 is closed. The battery voltage threshold level is the same for rising and falling edges. The filtering of glitches around the threshold voltage is achieved with a delay. In fact, once activated, the battery level should be lower than the threshold for a minimum amount of time before power-on reset block 118 de-asserts the reset signal.

Figure 3:
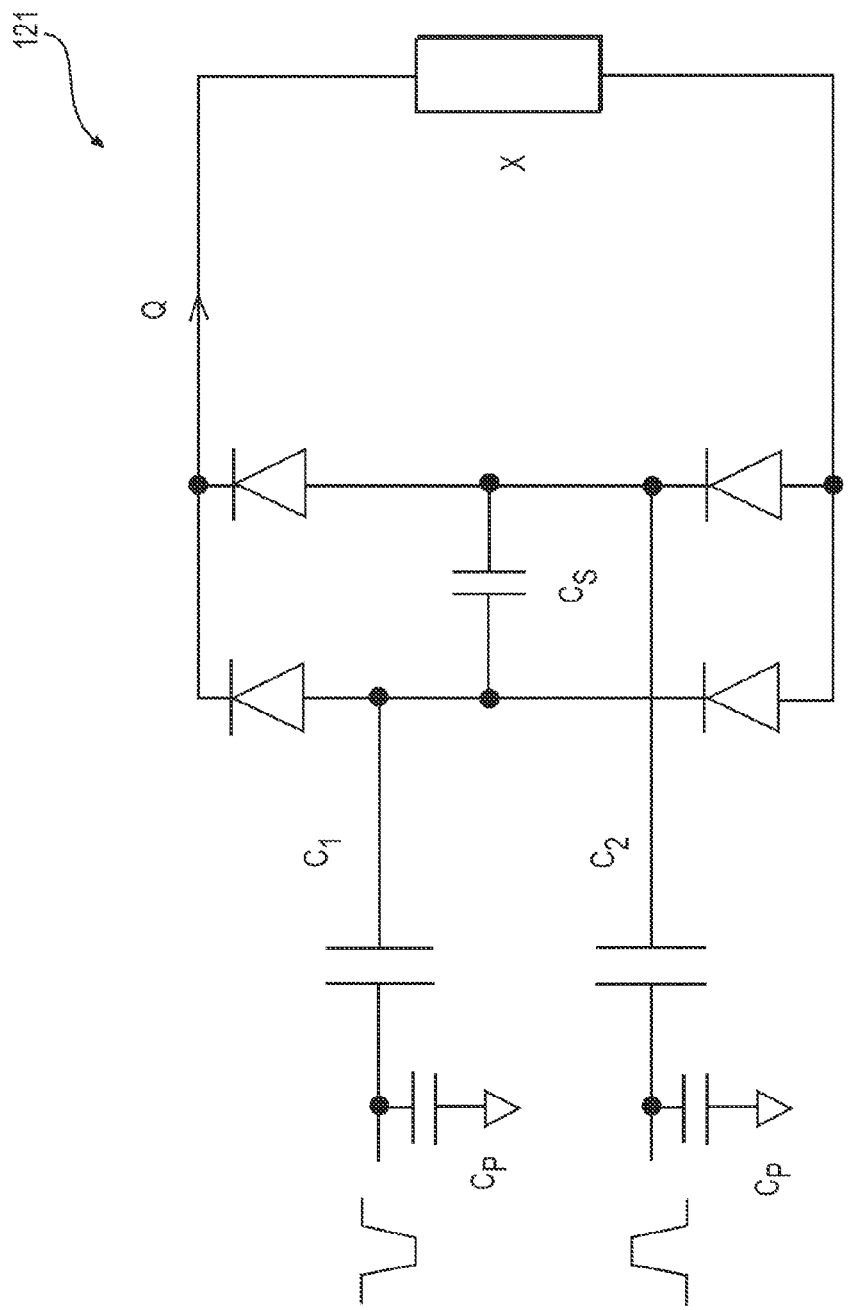
FIG. 3 is a circuit diagram of a charge pump suitable for use in the ASICs of FIGS. 1 and 2.

The PLC 122 also drives a charge pump 121, shown in greater detail in FIG. 3, that steps up, or transforms, the low voltage from the battery to a high voltage suitable for actuating the electro-active element 140 with an actuator 123. For example, the charge pump 121 may step up a battery voltage of about 2 V to a 9 V level suitable for driving a liquid-crystal-based electro-active element. The charge pump 121 converts the DC battery voltage by periodically switching a ceramic or electrolytic capacitor with active switches. First, the switches flip to charge the capacitor by connecting it across a voltage source. Next, the switches connect the capacitor to the output in a way that produces a different voltage level, i.e., the higher voltage used to power the electro-active cell 140.

Figure 4:
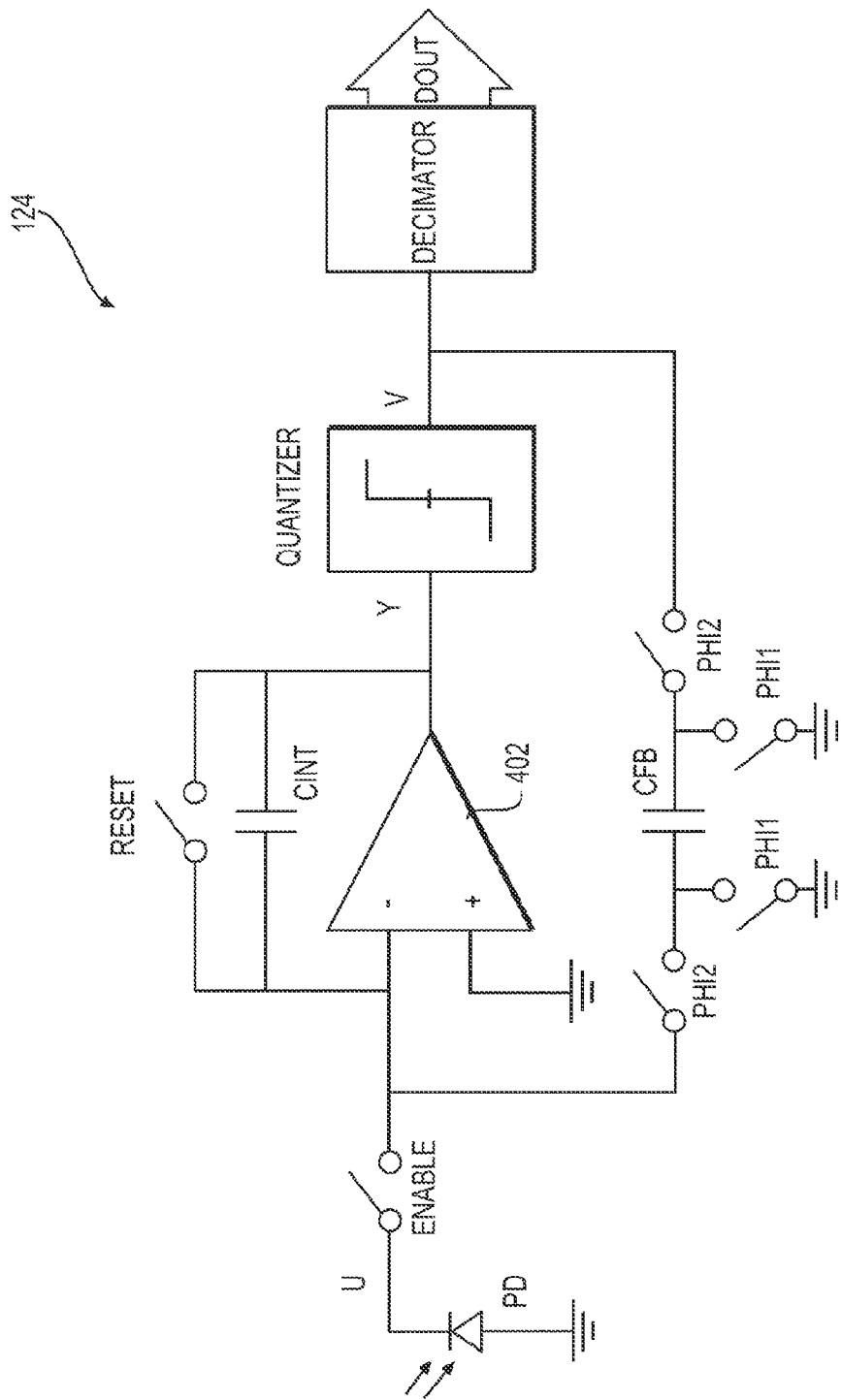
FIG. 4 is a circuit diagram of an analog-to-digital converter (ADC) suitable for use in the ASICs of FIGS. 1 and 2.

The PLC 122 is also coupled to a sigma-delta analog-to-digital converter (ADC) 124 that digitizes signals from the sensor 150, a bandgap block 125 that provides a reference voltage to the ADC 124, and a clock 128. In operation, the ADC 124, which is shown in greater detail in FIG. 4, digitizes an analog signal (e.g., a photocurrent) indicative of an accommodative response from the sensor 150 by comparing the analog to a reference signal generated by the bandgap block 125. The ADC 124 includes a programmable gain amplifier 402 and an auto-ranging function that automatically switches the analog level capture range.

Figure 5:
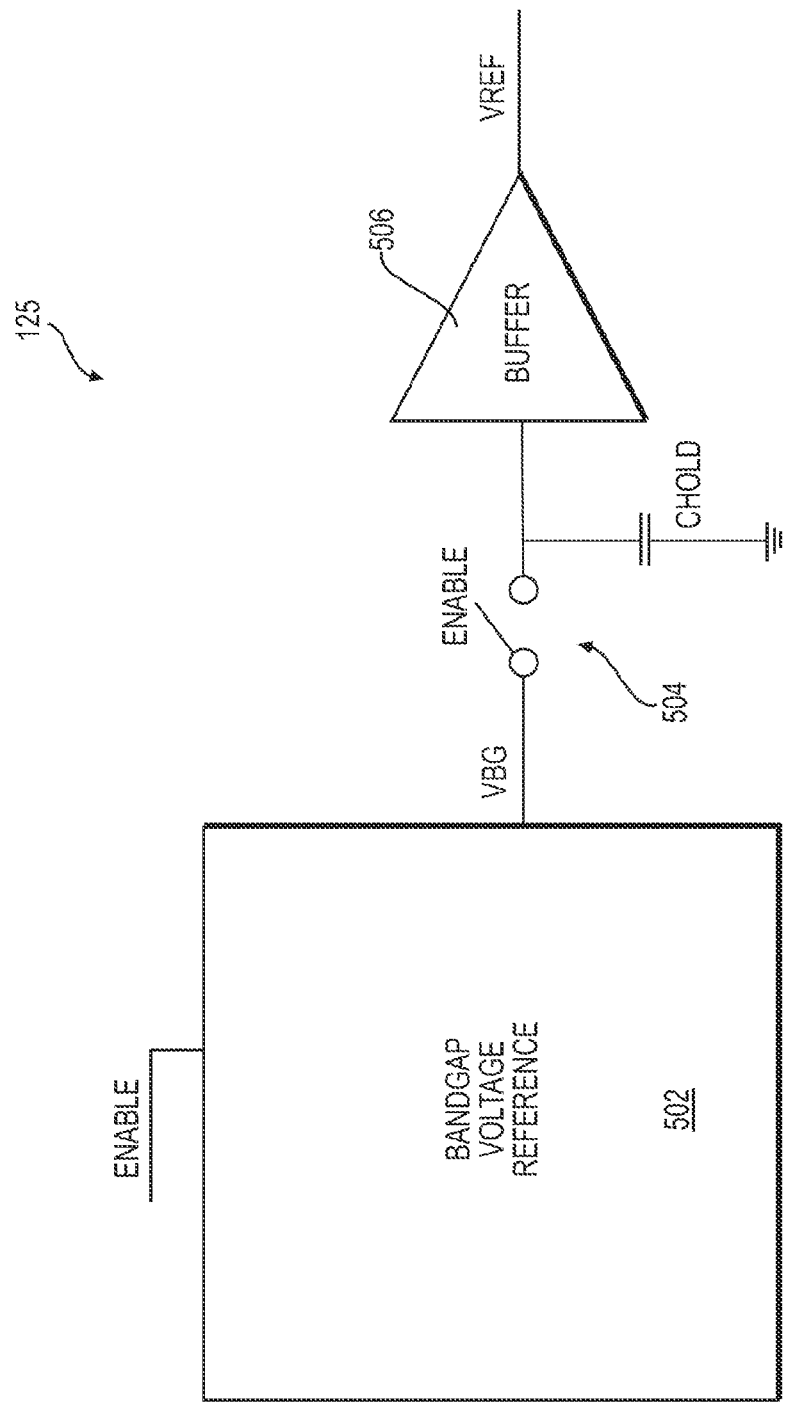
FIG. 5 is a circuit diagram of a bandgap block suitable for use in the ASICs of FIGS. 1 and 2.

As shown in FIG. 5, the bandgap block 125 includes a voltage reference 502 that is coupled to a buffer 506 via a switch 504. When the bandgap block 125 is enabled, the switch 504 opens, allowing the ADC 124 to sample and hold the reference signal while the bandgap block 125 is disabled to reduce power consumption. Ideally, the reference signal is independent of the battery voltage and the device temperature to provide a consistent response to accommodative triggers. The ADC 124 transmits a digital signal indicative of the detected accommodative trigger to the PLC 122, which processes the digital signal through an algorithm or logic as described below. The PLC 122 retrieves data maintained in a look-up table in the memory 112 and determines the appropriate setting for the electro-active element 140 based on the digital signal and the data from the look-up table. The PLC 122 then uses an drives the charge pump 121 and the actuator 123 to set the electro-active element 140 appropriately.

Figure 6:
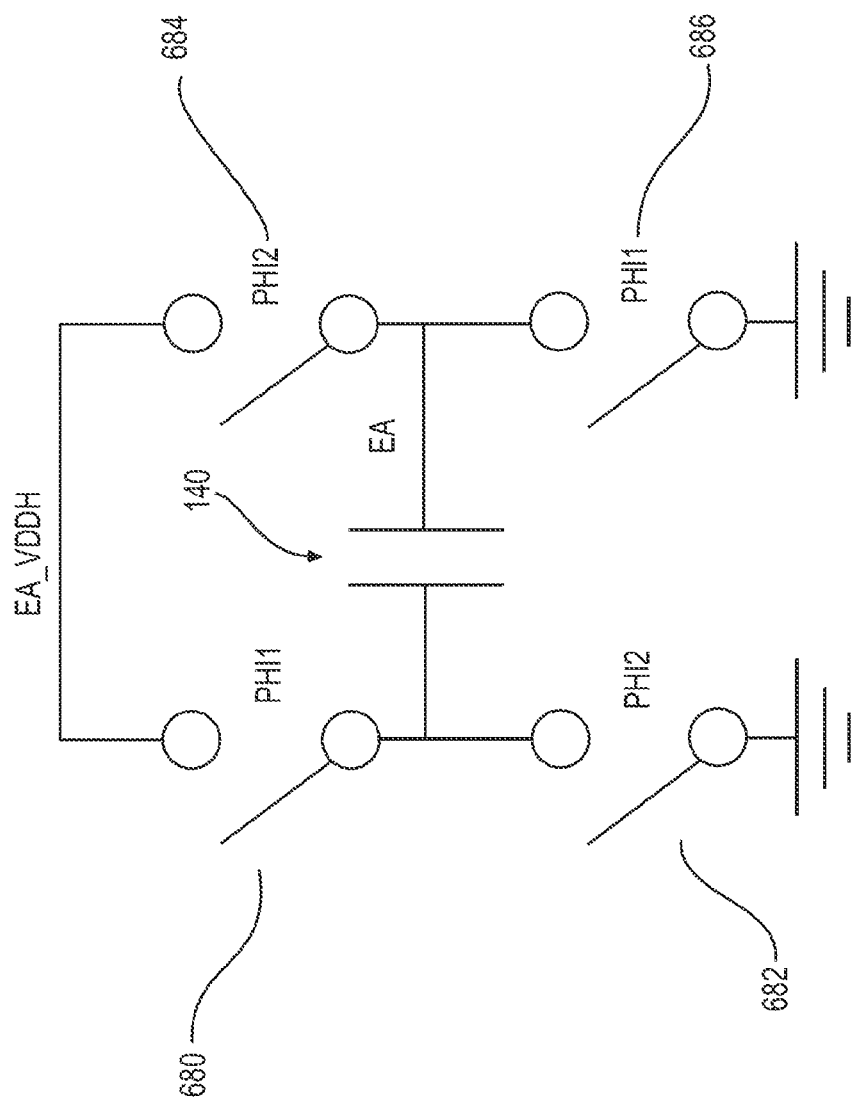
FIG. 6 shows the actuator of FIG. 2.

For instance, the sensor 150 may detect a decrease in pupil size, but no change in ambient light level, indicating that the patient is attempting to focus on a near object. The ADC 124 digitizes photocurrent from the sensor 150 to provide a digital signal whose amplitude indicates the desired degree of accommodation. (In some cases, the ADC 124 may amplify the signal level by a predetermined gain.) The PLC 122 uses the digital signal to select an appropriate setting for the electro-active element 140 from among pairs of accommodation values and corresponding electro-active element settings stored in a look-up table in the memory 112. The PLC 122 drives the charge pump 121, which in turn drives the actuator 123, shown in FIG. 6 as an H bridge circuit, to increase the optical power and/or depth of field by actuating the electro-active element 140, which is shown as a capacitive load in FIG. 6. When the switches 680 and 686 are closed (and switches 682 and 684 are open) a positive voltage is applied across the electro-active element 140. By opening switches 680 and 686 and closing switches 682 and 684, this voltage is reversed.

Figure 7:
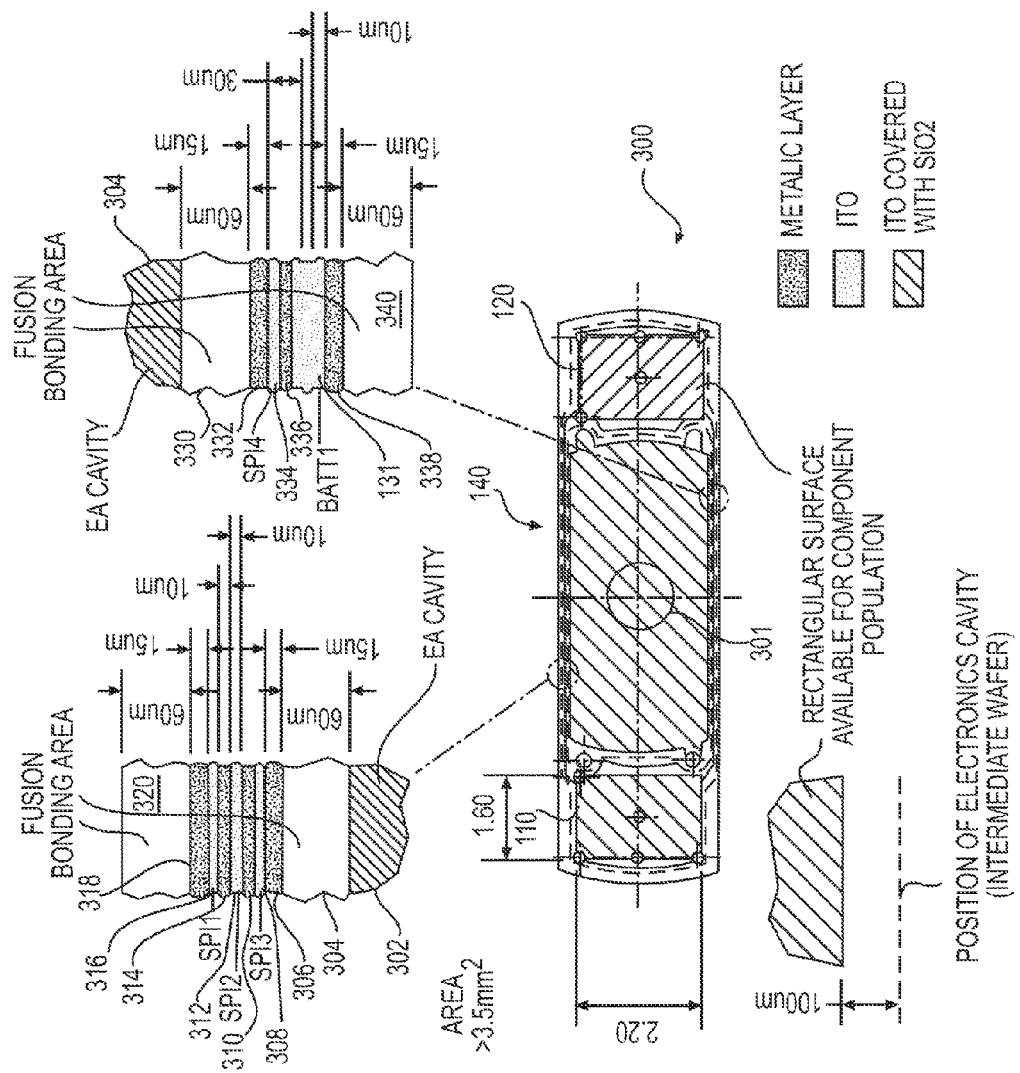
FIG. 7 shows plan and elevation views of the rechargeable battery, first application-specific integrated circuit (ASIC), second ASIC, and electro-active element of FIG. 1.

FIG. 7 shows plan and perspective cutaway views that illustrate the construction of an assembly 300 that includes the first ASIC 110, second ASICs 120, and electro-active cell 140. The assembly 300 may be embedded in or affixed to an implantable optic, such as a spherical lens, to form the implantable ophthalmic device 100 shown in FIG. 1. The assembly 300 includes electro-active material 302, such as liquid crystal material, disposed about a fixed aperture 301 centered on the optical axis of the assembly 300. The fixed aperture 301 defines a limit on the aperture diameter range (and depth of field range) provided by the electro-active element 130. Pads for the first and second ASICs 110 and 120 are disposed on either side of the electro-active element 140 and sandwiched between the substrates described below. The ASIC pads may be populated with various electronic components, including those described with respect to FIG. 2A. The ASICs 110, 120 communicate with each other via various SPI layers disposed between the substrates and draw power from the battery 130 via a battery contact line 131.

The electro-active material 302 is contained within a cavity bounded by an upper glass or plastic substrate 304 and a lower glass or plastic substrate 330. The upper substrate 304 is coated with: a first metal layer 306, a first SPI layer 308, a first indium tin oxide (ITO) layer 310, a second SPI layer 312, a first $SiO_x$ layer 314, a third SPI layer 316, a second metal layer 318, and an outer glass substrate 320 which is about 60 µm thick. Similarly, the lower substrate 330 is coated with a third metal layer 332, a fourth SPI layer 334, and a second ITO layer 336. The battery contact line 131 is sandwiched between the second ITO layer 336 and a second $SiO_x$ layer 338, which is disposed adjacent to another outer substrate 340.

The SPI, metal, ITO, and SiOx layers on either side of the electro-active material 302 are each about 10-15 µm thick, and each substrate is about 60 µm thick. The entire assembly 300 is about 2.20 mm wide and about 5.80 mm long. Each ASIC 110, 120 has an area of less than about 3.5 $mm^2$. In general, each ASIC 110, 120 should have an area of about 2 mm×2 mm or less, e.g., about 1.75 mm×1.75 mm. The ASICs 110 and 120 may be different sizes, e.g., the first ASIC 110 may be about 3.15 $mm^2$, whereas the second ASIC 120 may be about 2.75 $mm^2$.

The assembly 300 can be embedded in or affixed to an intraocular lens (IOL), intraocular optic (IOO), corneal inlay, corneal onlay, or other implantable ophthalmic device. Implantable ophthalmic devices, such as the device 100 of FIG. 1, may be inserted or implanted in the anterior chamber or posterior chamber of the eye, into the capsular sac, or the stroma of the cornea (similar to a corneal inlay), or into the epithelial layer of the cornea (similar to a corneal onlay), or within any anatomical structure of the eye. When implanted, the first and second ASICs 110, 120 may be disposed out of the patient's line of sight, e.g., in the vicinity of the haptic/optic junction.

In cases where the implantable ophthalmic device is an IOL, the IOL may have at least one static optical power provided by a curved surface and/or a graded index profile. Such an IOL also includes an electro-active element that acts as a dynamic aperture that, when actuated, alters the patient's depth of field as described in U.S. Pat. No. 7,926,940 to Blum et al., which is incorporated herein by reference in its entirety. Alternatively, the implantable ophthalmic device may be an IOO, which has little to no optical power, but also include a dynamic aperture that provides an increased depth of field. In some illustrative devices with dynamic apertures, opening and closing the aperture serves to provide a continuous range of focus between the fixed or static corrective powers of the ophthalmic lens.

Power Supplies for Use in Illustrative Ophthalmic Devices

As noted above, the first ASIC 110 and second ASIC 120 draw electrical power from a power supply, such as a solar cell, capacitor, or thin-film rechargeable battery like those manufactured by Excellatron, Wyon, or Front Edge. In FIG. 1, for example, a rechargeable battery 130 coupled to the first and second ASICs 110 and 120 provides power for the ASICs 110 and 120 and for the electro-active element 140. Thin-film rechargeable batteries are particularly well-suited for use in implantable ophthalmic devices because that can be cycled more 45,000 times, which could translate to a usable lifetime of 20-25 years in the lens or optic. Two thin film rechargeable batteries may be used and may stacked one atop the other. In this configuration, one of the batteries may be used for 20-25 years and the other battery may be switched to when the first battery is no longer operable. Alternatively, the other battery may be switched to by a signal sent remotely to the controller. This may extend the lifetime of the optic or lens to 40-50 years.

One or more light-sensitive cells, such as solar cells or photovoltaic cells, may also be used to supplement, augment, and/or obviate the need for a battery. The light-sensitive cell is located out of the user's line of sight of the user, e.g., peripheral to the margin of the pupil when partially dilated by darkness, but not fully dilated. The device may thus be charged by using an eye-safe laser capable of energizing the light-sensitive cell or cells.

Alternatively, the light-sensitive cell may be located in front of (closer to the cornea of the eye) and separately disposed from a portion of the iris of a user's eye. Thin electrical wiring may operably connect the solar cell to the ASICs. The electrical wiring may pass through the pupil without touching the iris and operably connect to the implantable ophthalmic device. The solar cell may be large enough such that it supplies enough electrical power to obviate the need for a separate power supply. The thin electrical wiring may not conduct electricity and may have a form factor which has the appropriate tensile strength to hold the solar cell in place. In some configurations, one or more small holes may be made in the iris by an ophthalmic laser such that the thin electrical wiring connects the solar cell to the implantable ophthalmic device.

Recharging Batteries in Illustrative Ophthalmic Devices

Figure 8:
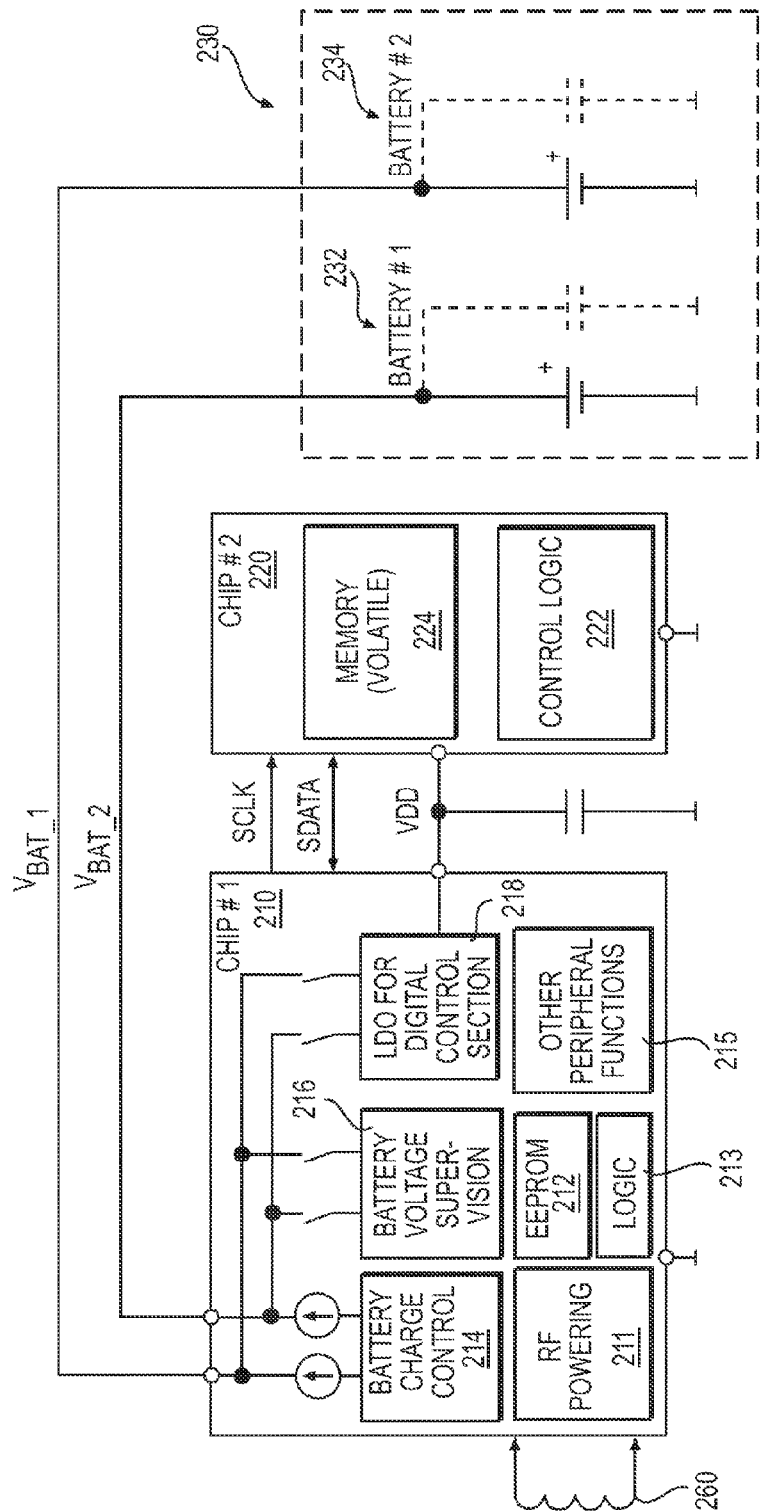
FIG. 8 illustrates alternative first and second ASICs suitable for use in the ophthalmic device of FIG. 1.

FIG. 8 shows an alternative first ASIC 210, an alternative second ASIC 220, and alternative power supply 230 suitable for use in the ophthalmic devices disclosed herein, including the device 100 of FIG. 1. The first ASIC 210 includes a memory 212 that stores actuation information for the electro-active element (not shown), logic 213, an low-dropout voltage regulator for the digital control section, and components 215 for other peripheral functions. The second ASIC 220 includes control logic 222 (e.g., a PLC) and volatile memory 224.

Figure 9:
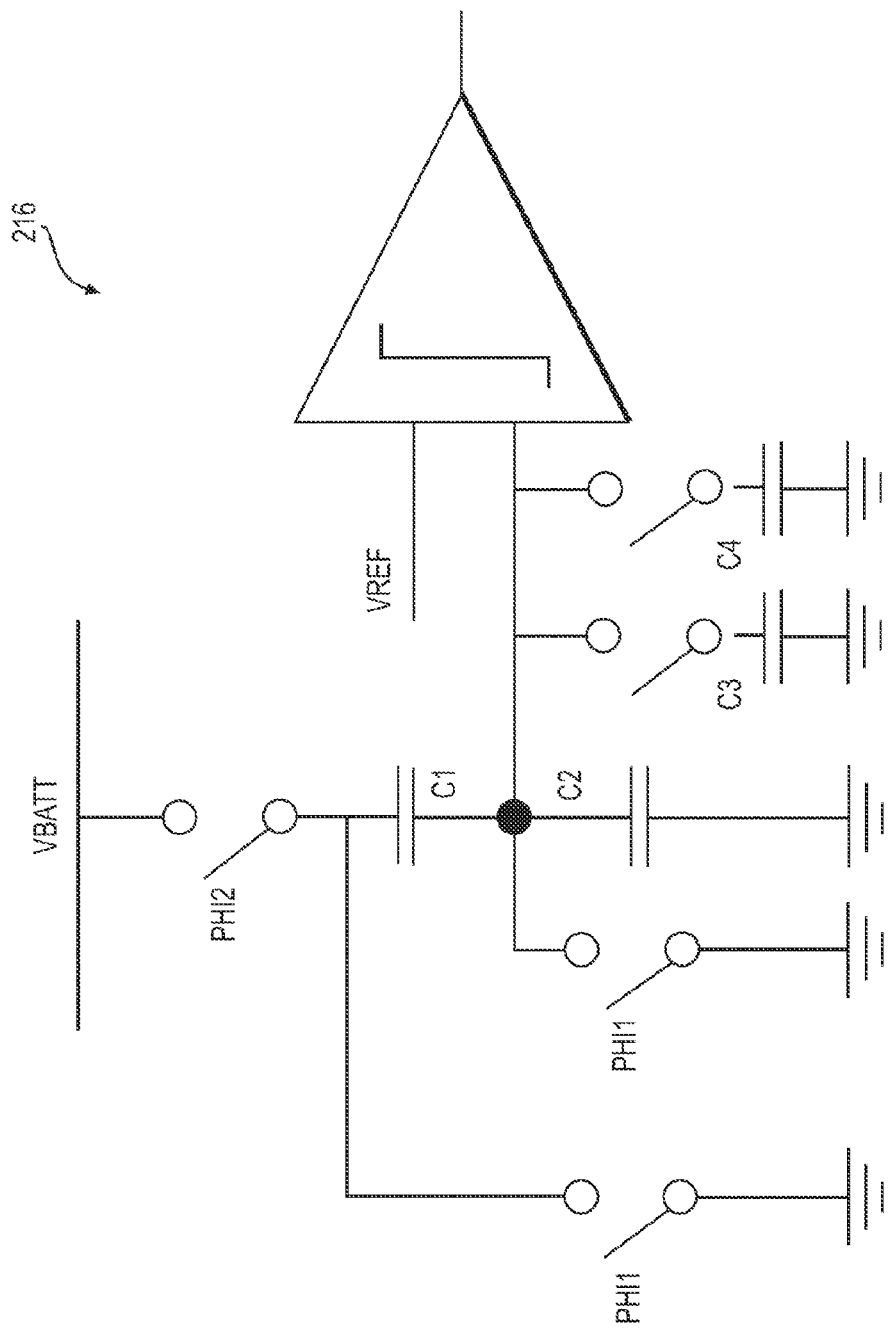
FIG. 9 shows the battery level monitor of FIG. 8.

The first ASIC 210 also includes components to monitor and charge the power supply 230, which includes two separate rechargeable batteries 232 and 234. A battery level monitor 216, shown in greater detail in FIG. 9, monitors the state of charge of each battery 232, 234 in the power supply 230. As shown in FIG. 9, the battery level monitor 216 includes a capacitor divider to save cross currents.

Figure 10:
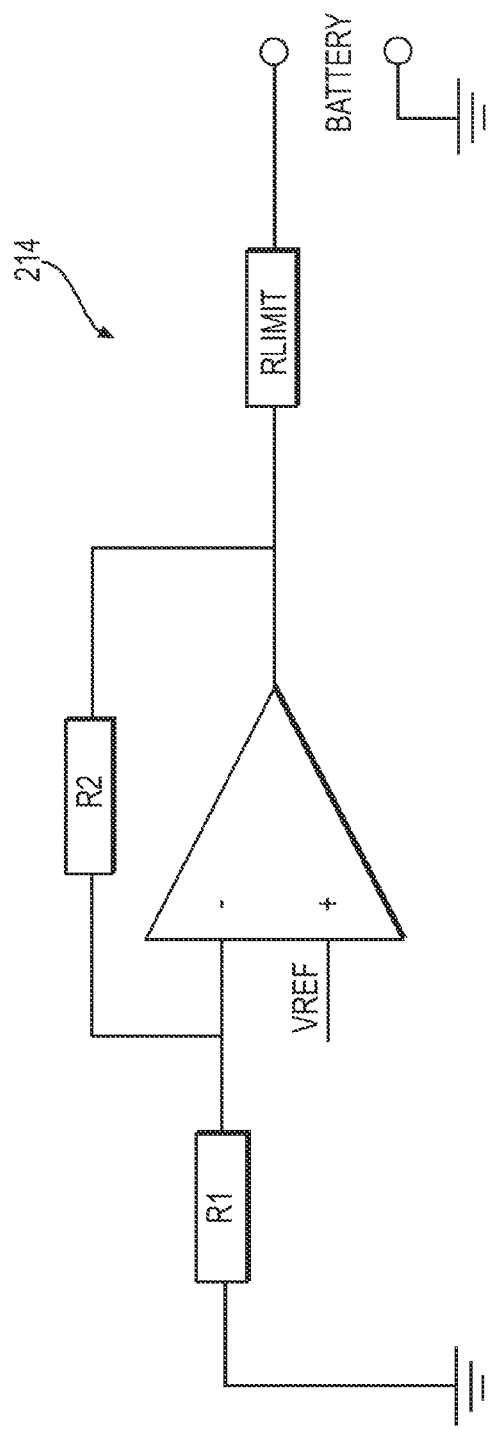
FIG. 10 shows the battery charger of FIG. 8.
Figure 16:
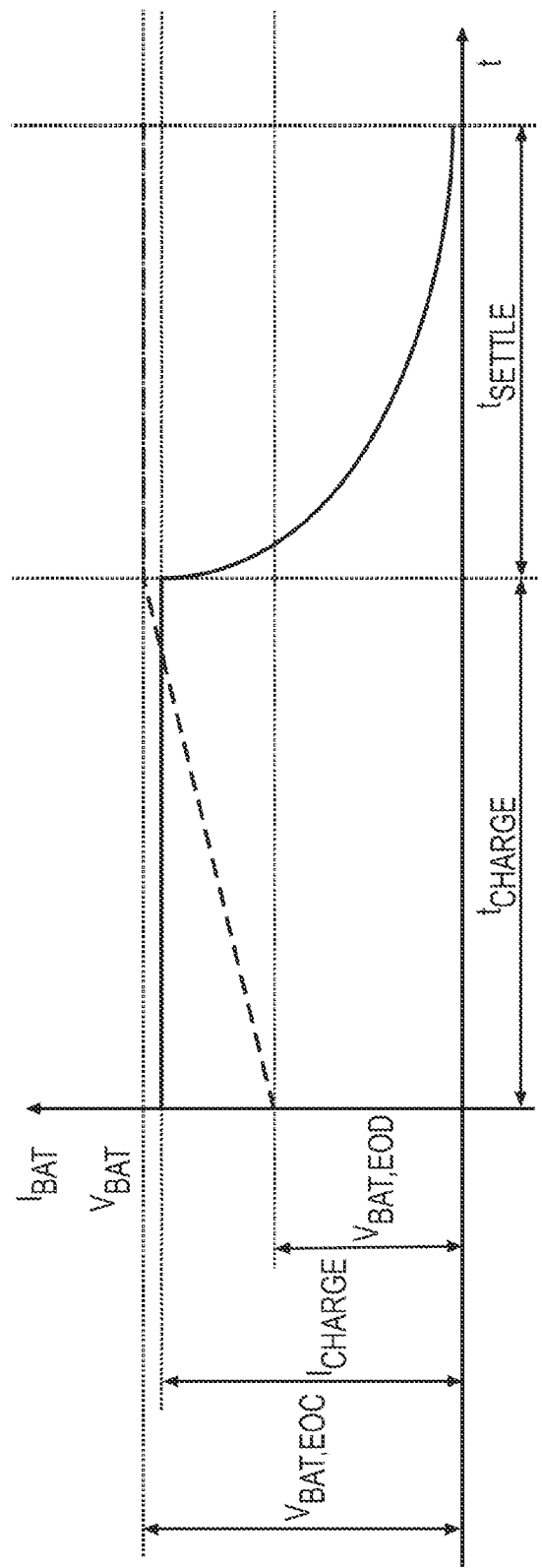
FIG. 16 is a plot of current and voltage versus time during an illustrative battery charging cycle.

When the battery level monitor 216 senses that a battery 232, 234 is undercharged, it triggers a battery charger 214, shown in greater detail in FIG. 10. For example, the battery level monitor 216 may trigger the battery charger 214 when the battery voltage falls below a predetermined value, e.g., about 1.2 V. Once activated, the battery charger 214, which is powered inductively by an rf field, charges the battery according to the plot shown in FIG. 16. Once the battery charger 214 is activated, it enters a first phase in which it charges the undercharged battery with a constant current. The constant current can be trimmed within a predetermined range (e.g., about 120 µA to about 160 µA) if desired. Once the undercharged battery reaches a predetermined end-of-charge voltage, the battery charger 214 enters a second phase in which it charges the battery 130 at a fixed voltage, e.g., about 4.1 V to about 4.2 V, for a predetermined time. The predetermined end-of-charge voltage is programmable, and may be about 1.6 V to about 1.8 V. Once the predetermined time elapses, the battery charger 214 stops charging the now-charged battery to prevent overcharging.

Figure 11:
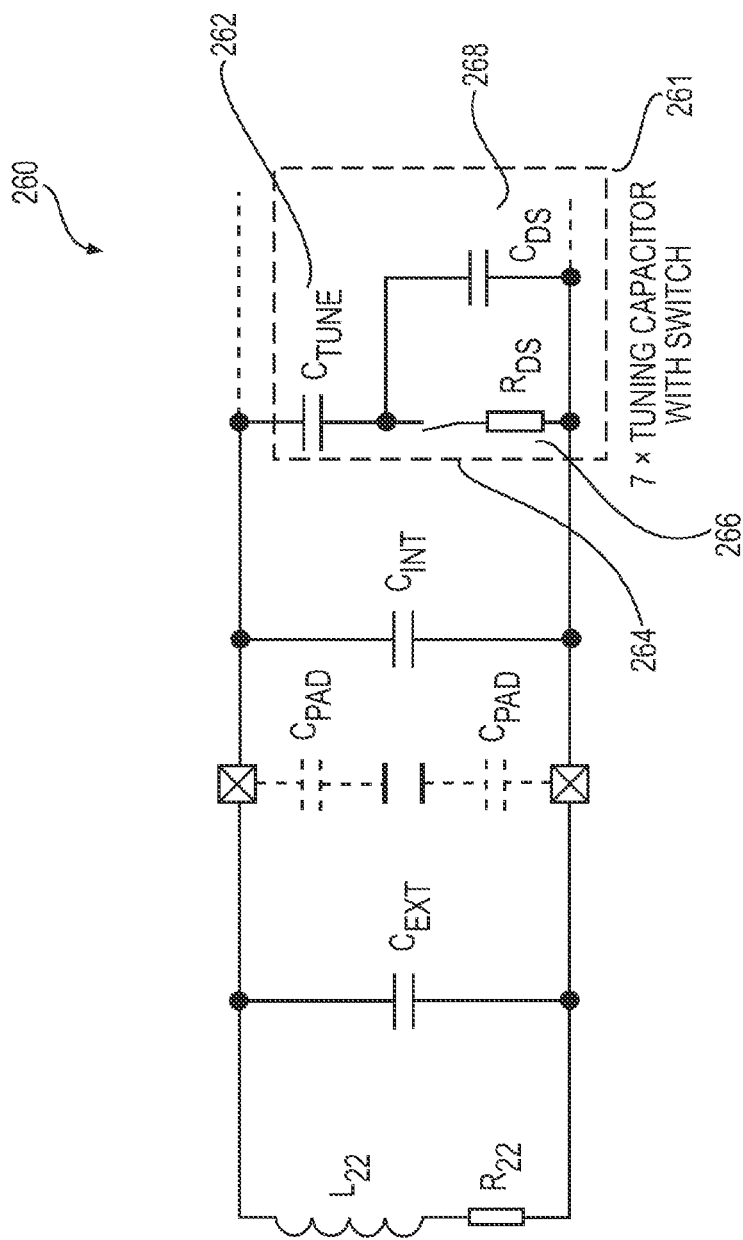
FIG. 11 shows a radio-frequency (rf) antenna suitable for inductively charging the batteries of FIG. 8.
Figure 12:
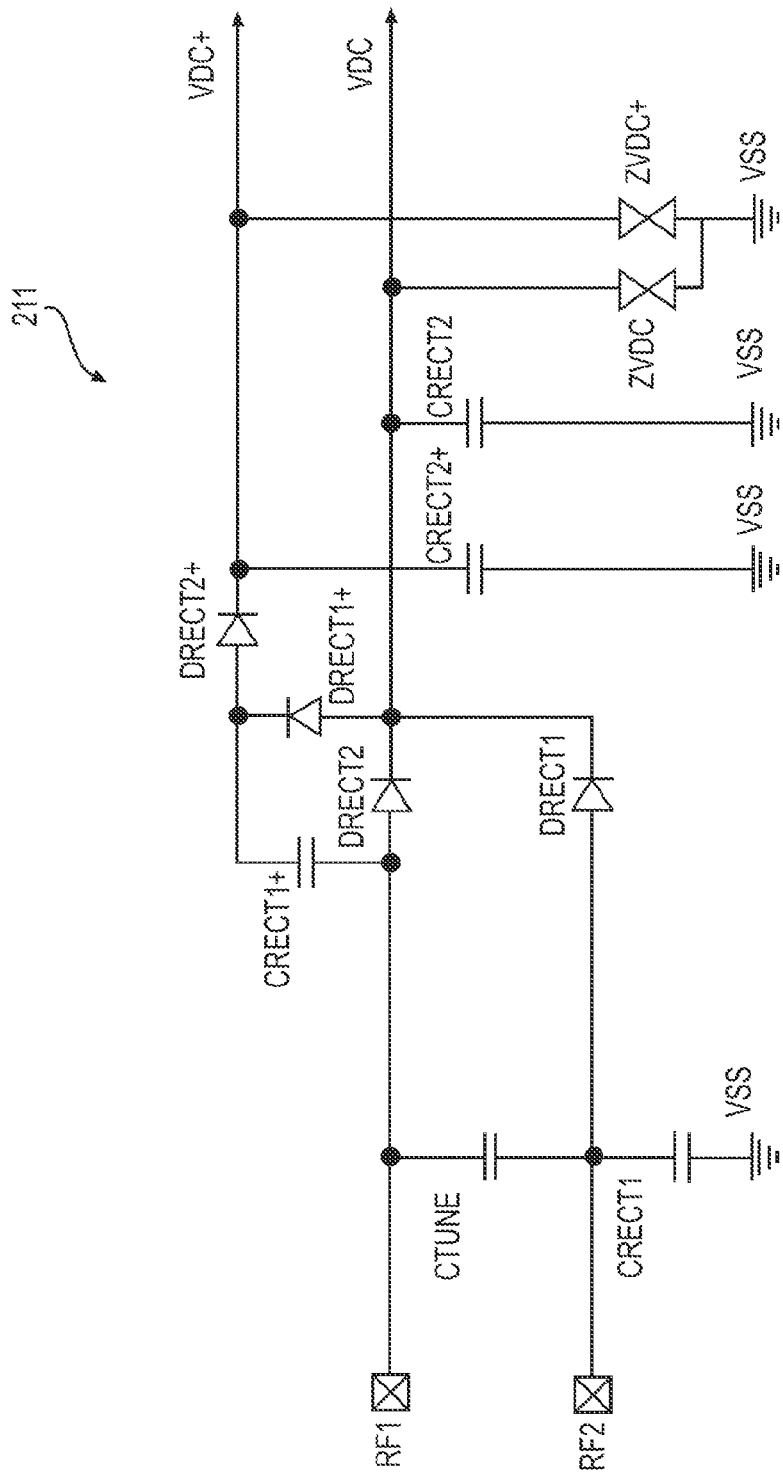
FIG. 12 shows a rectifier circuit suitable for harvesting a DC voltage to charge the batteries of FIG. 8.
Figure 13:
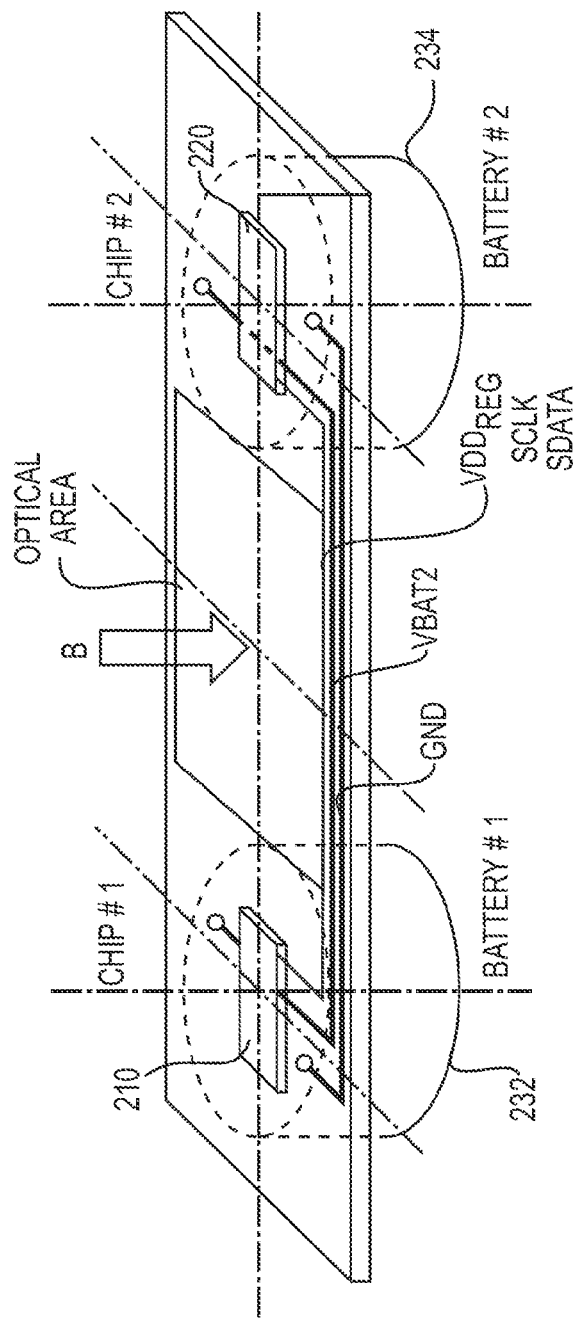
FIG. 13 illustrates inductive charging of the batteries of FIG. 8 using the rf antenna suitable of FIG. 11.

The battery charger 214 may draw power inductively via an rf antenna 260, shown in FIG. 11, which supplies current to the battery charger via a rectification circuit 211. The antenna 260 includes one or more trimming blocks 261, each of which includes a tuning capacitor 260 coupled in series with both a switch 262 and a load capacitor 268; the switch 262 and load capacitor 268 are in parallel. Closing the switch 262 connects the tuning capacitor 260 to a load 266, increasing the impedance to provide better power flow from an external power supply to the rectification circuit 211. The trimming blocks can be activated or de-activated as desired to optimize power flow. Once the rf antenna 260 is set appropriately, a magnetic field induces current flow in the device, and the rectification circuit, shown in FIG. 12, harvests a DC voltage for charging the batteries 232, 234. As shown in FIG. 13, the power (battery contact) lines run along the same side of the device to avoid formation of parasitic induction loops. For more on inductive charging, see U.S. application Ser. No. 12/465,970 entitled "Device for Inductive Charging of Implanted Electronic Devices," which is incorporated herein by reference in its entirety.

Operating States of Illustrative High-Voltage and Low-Voltage ASICs

The first and second ASICs can have four main power conditions corresponding to different device states, all of which are listed below in TABLE 1. When the system is off, the low-voltage ASIC is in an unpowered idle mode, and the high-voltage ASIC is in a sleep (shutdown) state. Under normally operating conditions, e.g., when the user is going about his or her day, the system operates in autonomous therapeutic function mode to provided automatic accommodation upon detection of accommodative responses. The second ASIC switches to its operational mode and the first ASIC remains in idle mode when the device is operating in autonomous therapeutic function mode. The device can also be charged and/or communicate wirelessly with external readers while continuing to provide autonomous therapeutic function for the patient. When charging and providing autonomous therapeutic function, the first ASIC switches to an externally (i.e., inductively) powered state and the second ASIC remains in its operational mode. The device may also be charged and/or communicate wirelessly without providing autonomous therapeutic function, in which case the second ASIC shuts down to minimize power consumption. In each case, the first ASIC can change the state of the second ASIC by issuing an "interrupt" signal (spi_vdd) to the second ASIC via an interchip data interface. If second ASIC is in a power-down state, the first ASIC initiates a power-on of the second ASIC and sets the interchip data interface into a command receive state.

TABLE 1

ASIC Powering Conditions

| Low-Voltage ASIC | High-Voltage ASIC | Device State |
|---|---|---|
| IDLE (unpowered) | Shutdown | System Off |
| IDLE (unpowered) | Operation | Autonomuous Therapeutical Function |
| RF powered (blank states in FIG. 14) | Operation | Charging or communication in progress, therapeutical function running |
| RF powered (blank states in FIG. 14) | Shutdown | Charging or communication in progress, therapeutical function disabled |

Figure 14:
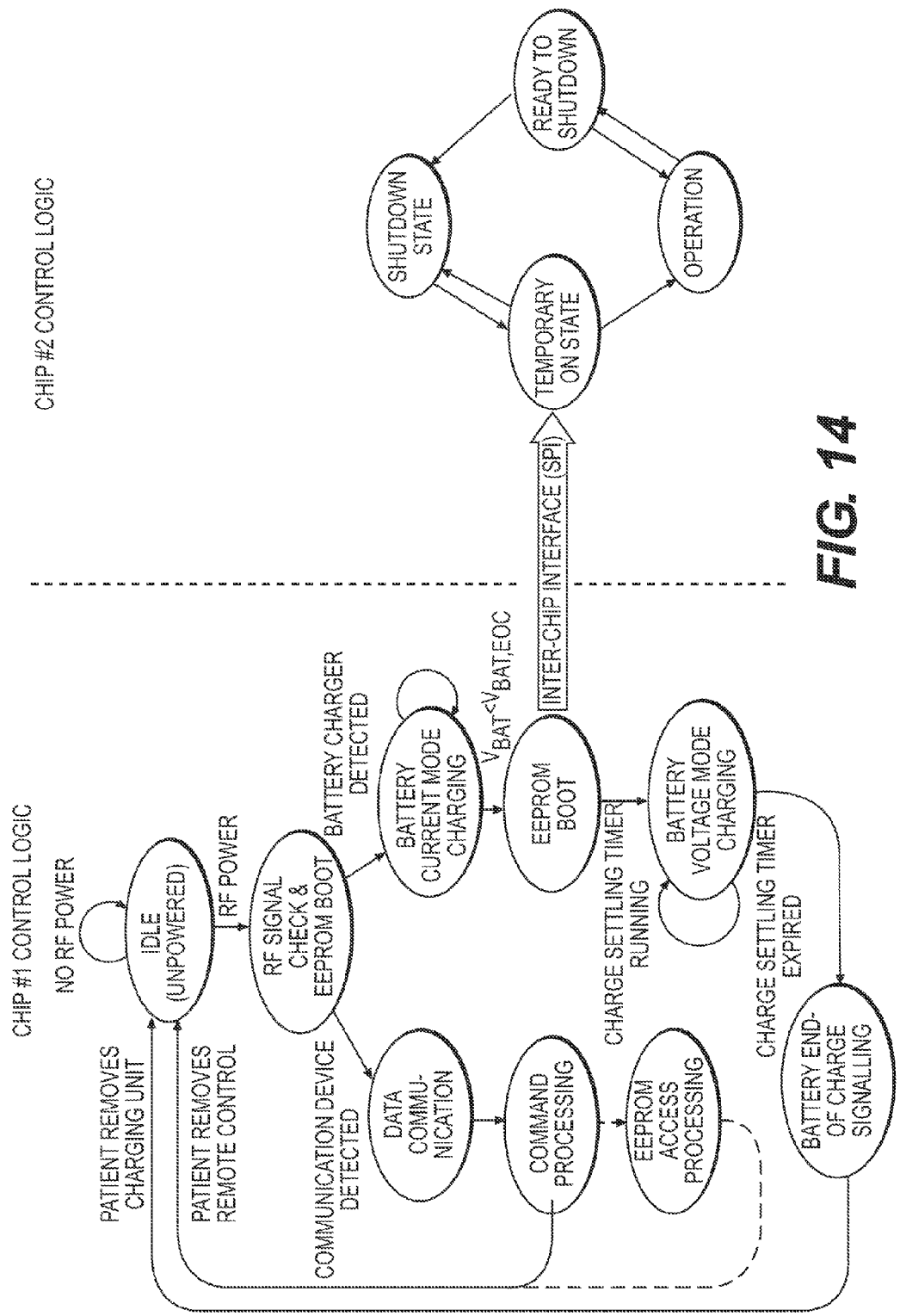
FIG. 14 is a state diagram that illustrates operation of illustrative first and second ASICs.

FIG. 14 is a state diagram that illustrates the control logic interaction between an exemplary first (low-voltage) ASIC and an exemplary second (high-voltage) ASIC. The first ASIC may transition from idle state to an operational state through application of an rf carrier signal to an rf front-end resonant circuit in the ophthalmic device. For example, the patient may use a remote control to actuate or upload new data to the ophthalmic device. Alternatively, the patient may charge the ophthalmic device with a charging unit.

When the rf front-end resonant circuit detects an rf carrier signal, it sends a signal to a control logic section block on the first ASIC. At the beginning of the application of an RF field, the control logic section block may be unaware of whether the rf field is being applied for communication and/or battery charging, or both. The logic section block checks the rf signal to determine whether to enter communication mode or battery charging mode. At the same time, a local memory (EEPROM) boot sequence is initiated to transfer the relevant control bits required on the first ASIC to local data latches. These bits may include trim bits for the rf tuning or control bits for battery charging.

If the logic section block determines that it should enter communication mode, it either begins data communication with the remote control, processes commands from the remote control, and stores/retrieves information from local memory. If the logic section block determines that it should enter charging mode, it begins constant current charging, then switches to constant voltage charging once the battery reaches a predetermined charge level as described above. Once communication or charging is finished, the patient removes the remote control or the charging unit, and the first ASIC returns to its idle state.

Examples of Electro-Active Elements

As used herein, the term "electro-active element" refers to a device with an optical property that is alterable as a function of space and/or time by the application of electrical energy. The alterable optical property may be, for example, optical power, which, for a lens, is the reciprocal of the focal length; refractive index (retardance); optical transmittance (transmissivity); diffraction efficiency; aperture size, shape, or position; or any combination thereof. An electro-active element may be constructed from two substrates and an electro-active material disposed between the two substrates. The substrates may be shaped and sized to ensure that the electro-active material is contained within the substrates and cannot leak out. One or more electrodes may be disposed on each surface of the substrates that is in contact with the electro-active material. When electrical energy is applied to the electro-active material by way of the electrodes, the electro-active material's optical property may be altered. For example, when electrical energy is applied to the electro-active material by way of the electrodes, the electro-active material's index of refraction may be altered, thereby changing the optical power of the electro-active element.

The electro-active element may be embedded within or attached to a surface of an optical element, such as a spherical lens, to form an electro-active lens. Alternatively, the electro-active element may be embedded within or attached to a surface of an optic which provides substantially no optical power to form an electro-active optic. In such a case, the electro-active element may be in optical communication with an aspheric optical element and/or a spherical optical element, but separated or spaced apart from or not integral with the aspheric optical element and/or the spherical optical element. The electro-active element may be located in the entire viewing area of the aspheric optical element and/or the spherical optical element or in just a portion thereof, e.g., near the top, middle or bottom portion of the lens or optic. The electro-active element may be capable of focusing light on its own.

Figure 15:
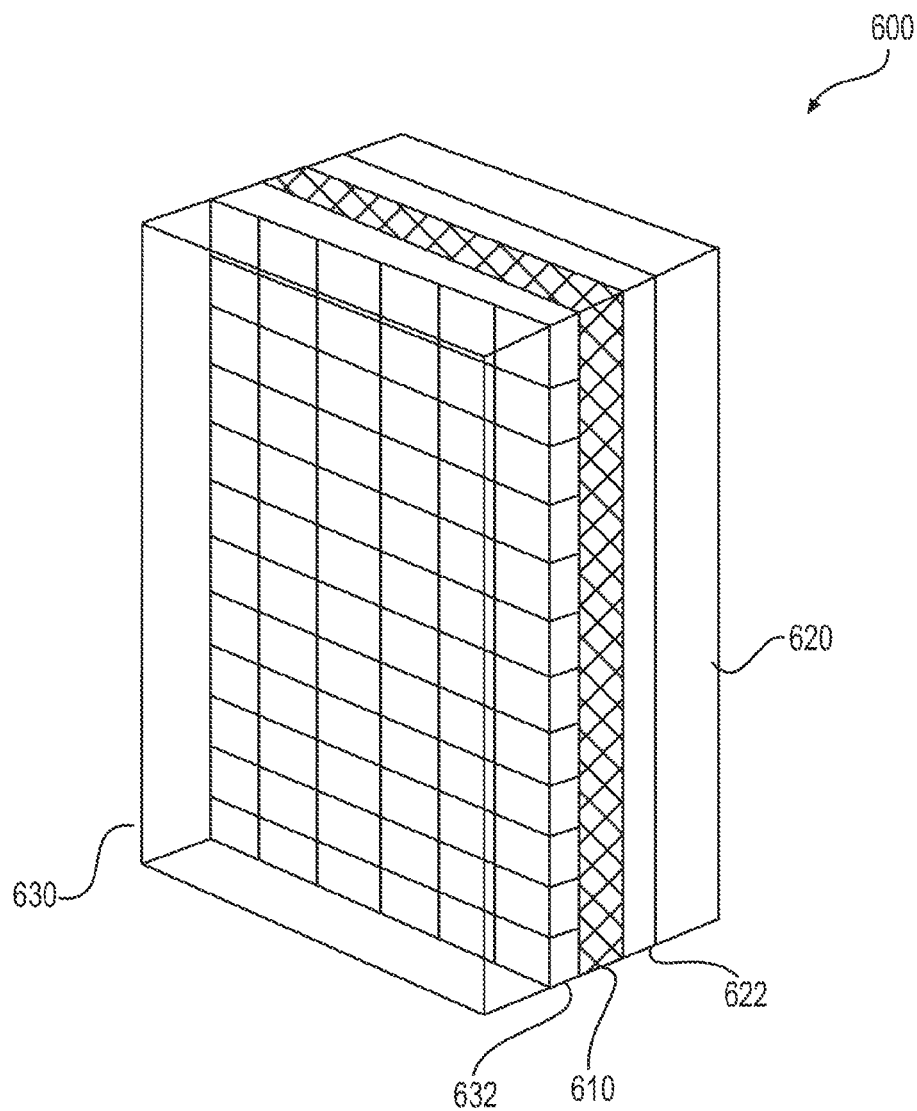
FIG. 15 shows an exemplary electro-active suitable for use with the ASICs of FIGS. 2 and 8.

FIG. 15 shows an electro-active element 600, which includes an electro-active material 610, such as liquid crystal material, sandwiched between two optical substrates 620 and 630. The thickness of the electro-active material 610 may be between 1 µm and 10 µm, and is preferably less than 5 µm. The substrates 620 and 630 may be substantially flat and parallel, curved and parallel, or one substrate may have a surface relief diffractive pattern and the other substrate may be substantially smooth. The substrates 620 and 630 may provide an optical power or the substrates may have no optical power. Each substrate may have a thickness of 200 µm or less and may be rigid or flexible. Exemplary rigid substrate materials include glass and silicon. Exemplary flexible substrates include flexible plastic films. In general, thinner substrates allows for a higher degree of flexibility for the electro-active element, which may be important for devices that are inserted or implanted into the eye.

A continuous optically transparent electrode 622 that provides for an electrical ground may be disposed on one of the substrates and one or more individually addressable optically transparent electrodes 632 may be disposed on the second substrate. Each electrode 632 defines the size, shape, and/or diameter of a corresponding pixel 642 in the electro-active device. Exemplary pixels may have an area of about 0.25 µm$^2$ each with a pixel pitch of about 0.5 µm. Alternatively, pixels may be arranged as concentric rings, arcs, rectangles, or any combination of suitable shapes. One or more of the electrodes 622 and 632 may also form structures that diffract incident light in a fixed pattern or manner. Electrodes 622 and 632 may, for example, comprise a transparent conductive oxide, such as indium tin oxide (ITO), or a conductive organic material, such as poly(3,4-ethylenedioxythiophene)poly(styrenesulfonate) (PEDOT:PSS) or carbon nano-tubes. The thickness of the optically transparent electrodes may be, for example, less than 1 µm, and is preferably less than 0.1 µm. One or more of the electrodes 622 and 632 may be coated with an alignment layer (not shown), with the electro-active material 610 disposed between the alignment layers.

Activating an electrode 632 of combination of electrodes 632 causes respective subsections, or pixels, in the electro-active element 600 to change state. For instance, one or more pixels in the electro-active device may have a transmissivity that varies from about 30% to about 99% in response to an applied voltage. Alternatively, or in addition, one or more pixels in the electro-active device may have a refractive index that varies by up to about 0.1 in response to an applied voltage. The pixel states may be continuous (analog), binary (e.g., transmissive/opaque or high index/low index), or include several discrete values (e.g., 30% transmissive, 50% transmissive, 80% transmissive, etc.). Some electro-active materials, including some liquid crystal materials, remain in active states for only as long as they experience an applied voltage. Other electro-active materials are bi-stable: applying a voltage causes them to switch from one state to another, but no voltage is required to keep them in their current state. Bi-stable electro-active materials are especially attractive for use in implantable ophthalmic device because they consume power only when being switched.

Examples of Sensors for Use in Ophthalmic Device

As described above, an illustrative ophthalmic devices may include a sensor to measure or infer the distance to the object(s) that the user is trying to focus on. The sensor may be operably (e.g., wirelessly or electrically) coupled to processor and may provide an indication of the object distance and/or pupil size to the processor. The sensor may include one or more sensing elements, such as a range finder for detecting a distance to which a user is trying to focus and/or a light-sensitive cell for detecting light that is ambient and/or incident to the implantable ophthalmic device. Suitable light-sensitive cells include, but are not limited to photodetectors, photovoltaic cells, and ultraviolet- or infrared-sensitive photo cells. Other suitable sensing elements include, but are not limited to a tilt switch, a passive range-finding device, a time-of-flight range finding device, an eye tracker, a view detector, an accelerometer, a proximity switch, a physical switch, a manual override control, a capacitive switch that switches when a user touches the nose bridge of a pair of spectacles, a pupil diameter detector, a bio-feed back device connected to an ocular muscle or nerve, or the like. The sensor may also include one or more micro electro mechanical system (MEMS) gyroscopes adapted for detecting a tilt of the user's head or encyclorotation of the user's eye.

An illustrative sensor may include two or more photo-detector arrays with a focusing lens placed over each array. Each focusing lens may have a focal length appropriate for a specific distance from the user's eye. For example, three photo-detector arrays may be used, the first one having a focusing lens that properly focuses for near distance, the second one having a focusing lens that properly focuses for intermediate distance, and the third one having a focusing lens that properly focuses for far distance. A sum of differences algorithm may be used to determine which array has the highest contrast ratio (and thus provides the best focus). The array with the highest contrast ratio may thus be used to determine the distance from a user to an object the user is focusing on.

When the sensor detects changes in object distance, pupil size, and/or intensity, it sends a signal to the processor which triggers the activation and/or deactivation of the electro-active element in the implantable ophthalmic device. For example, the sensor may detect the intensity of light and communicate this information to the processor. If the sensor detects that a user is focusing within a near distance range, the processor may cause the electro-active element to increase its optical power. If the sensor detects that the user is focusing beyond the near distance range, the processor may cause the electro-active element to decrease its optical power. The processor may have a delay feature which ensure that a change in intensity of light is not temporary (i.e., lasts for more than the delay of the delay feature). Thus, when a user blinks his or her eyes, the size of the aperture will not be changed since the delay of the delay circuit is longer than the time it takes to blink. The delay may be longer than approximately 0.0 seconds, and is preferably 1.0 seconds or longer.

Some configurations may allow for the sensor and/or processor to be overridden by a manually operated remote switch. The remote switch may send a signal by means of wireless communication, acoustic communication, vibration communication, or light communication such as, by way of example only, infrared. By way of example only, should the sensor sense a dark room, such as a restaurant having dim lighting, the controller may cause the dynamic aperture to dilate to allow more light to reach the retina. However, this may impact the user's ability to perform near distance tasks, such as reading a menu with small print. For instance, the user could remotely control the electro-active element of the implantable ophthalmic device to change the optical power and/or to increase the depth of field and enhance the user's ability to read the menu. When the near distance task has completed, the user may remotely allow the sensor and controller to cause the electro-active element to revert back to its previous optical power and/or depth of field settings. For more on electrical, optical, and mechanical sensors, see U.S. Pat. No. 7,926,940 to Blum et al., which is incorporated herein by reference in its entirety.

Alternatively, the sensor can include an electrochemical detector that monitors the changes in ion concentration in the eye, e.g., in the ocular cytosolic fluid. As understood by those skilled in the art, the accommodative response (also known as the accommodative loop) includes at least three involuntary ocular responses: (1) ciliary muscle contraction, (2) iris sphincter contraction (pupil constriction increases depth of focus), and (3) convergence (looking inward enables binocular fusion at the object plane for maximum binocular summation and best stereoscopic vision). Both the ciliary muscle and the iris sphincter are smooth muscles whose relaxation and contraction is regulated by an ion channel that carries calcium, sodium, potassium, phosphate, magnesium, zinc, or any other suitable ion. When an accommodative impulse causes the ciliary muscle and/or the iris sphincter relax and/or contract, the ion concentration in the ion channel changes by amount or differential that can be measured by the electrochemical detector, which emits an electrical signal in response to the change in ion concentration. For more on accommodative triggers and sensors, see U.S. application Ser. No. 12/496,838 to Gupta et al., entitled "Sensor for Detecting Accommodative Trigger" and filed on Jul. 2, 2009, which is incorporated herein by reference in its entirety.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. An implantable ophthalmic device comprising:
   a high-voltage application-specific integrated circuit (ASIC) configured to actuate an electro-active element at a first voltage; and
   a low-voltage ASIC operably coupled to the high-voltage ASIC and configured to (i) regulate the high-voltage ASIC and (ii) operate at a second voltage lower than the first voltage.

2. The implantable ophthalmic device of claim 1 wherein the low-voltage ASIC is configured to regulate the high-voltage ASIC by causing the high-voltage ASIC to transition from an idle state to an operational state.

3. The implantable ophthalmic device of claim 1 wherein the second voltage is about 5 volts or less and the first voltage is about 5 volts to about 11 volts.

4. The implantable ophthalmic device of claim 1 further comprising:
   a power supply configured to supply current to at least one of the high-voltage and low-voltage ASICs at a power supply voltage equal to or less than the second voltage.

5. The implantable ophthalmic device of claim 4 wherein the high-voltage ASIC includes a charge pump to transform the power supply voltage to the first voltage.

6. The implantable ophthalmic device of claim 4 further comprising:
   a switch configured to enable current flow from the power supply to the high-voltage ASIC in response to a signal from the low-voltage ASIC; and
   a power-on reset block configured to reset the high-voltage ASIC in response to actuation of the switch.

7. The implantable ophthalmic device of claim 4 wherein the power supply includes a battery and further comprising a battery charger operably coupled to the battery and configured to charge the battery.

8. The implantable ophthalmic device of claim 7 further comprising:
   a radio-frequency (rf) antenna operably coupled to the battery charging and configured to couple rf energy to the battery charger;
   a resonating capacitor in series with the rf antenna to provide an impedance for altering power transfer characteristics of the rf antenna; and
   a tuner to trim the resonating capacitor.

9. The implantable ophthalmic device of claim 7 wherein the battery charger is configured to charge the battery by:
   (i) charging the battery at a constant current until the battery reaches a predetermined voltage; and
   (ii) charging the battery at a constant voltage for a predetermined time after the battery reaches the predetermined voltage.

10. The implantable ophthalmic device of claim 9 wherein the constant current is about 120 µA to about 180 µA.

11. The implantable ophthalmic device of claim 9 wherein the predetermined voltage is about 1.6 V to about 1.8 V.

12. The implantable ophthalmic device of claim 4 wherein the power supply includes a solar cell.

13. The implantable ophthalmic device of claim 1 wherein at least one of the high-voltage and low-voltage ASICs includes a nonvolatile memory configured to store information for actuating the electro-active element.

14. The implantable ophthalmic device of claim 1 wherein at least one of the high-voltage and low-voltage ASICs includes a programmable logic controller to determine an actuation state of the electro-active element based on an accommodation signal representative of an accommodative response of a patient's eye.

15. The implantable ophthalmic device of claim 14 wherein at least one of the high-voltage and low-voltage ASICs includes an analog-to-digital converter (ADC) configured to convert an analog signal from a sensor into the accommodation signal.

16. The implantable ophthalmic device of claim 15 wherein at least one of the high-voltage and low-voltage ASICs further includes a bandgap block configured to provide a reference voltage that is independent of both temperature and a power supply voltage to the ADC.

17. The implantable ophthalmic device of claim 1 wherein at least one of the high-voltage and low-voltage ASICs has a length of about 2 mm or less or and a width of about 2 mm or less.

18. The implantable ophthalmic device of claim 1 wherein the high-voltage and low-voltage ASICs are hermetically sealed.

19. An implantable ophthalmic device comprising:
   a power supply configured to supply current at a first voltage to a low-voltage application-specific integrated circuit (ASIC) and a high-voltage ASIC;
   a charge pump operably coupled to the power supply and configured to transform the first voltage to a second voltage that is greater than the first voltage and suitable for actuating an electro-active element; and
   a battery charger operably coupled to the battery and configured to charge the battery:
   (i) at a constant current until the battery reaches a predetermined voltage; and
   (ii) at a constant voltage for a predetermined time after the battery reaches the predetermined voltage.

* * * * *

UNITED STATES PATENT AND TRADEMARK OFFICE
CERTIFICATE OF CORRECTION

PATENT NO.         : 9,259,309 B2
APPLICATION NO.    : 13/805612
DATED              : February 16, 2016
INVENTOR(S)        : Jean-Noel Fehr, Walter Doll and Urban Schnell It is certified that error appears in the above-identified patent and that said Letters Patent is hereby corrected as shown below:

ON THE TITLE PAGE

Item 73 (Assignee), delete "CA" and insert --VA--.

Signed and Sealed this
Twenty-fourth Day of May, 2016

Michelle K. Lee
*Director of the United States Patent and Trademark Office*